United States Patent [19]
Blumberg et al.

[11] Patent Number: 6,086,875
[45] Date of Patent: Jul. 11, 2000

[54] RECEPTOR SPECIFIC TRANSEPITHELIAL TRANSPORT OF IMMUNOGENS

[75] Inventors: Richard S. Blumberg, Chestnut Hill; Neil E. Simister, Wellesley; Wayne L. Lencer, Jamaica Plain, all of Mass.

[73] Assignees: The Brigham and Women's Hospital, Inc., Boston; Brandeis University, Waltham, both of Mass.

[21] Appl. No.: 08/374,159

[22] Filed: Jan. 17, 1995

[51] Int. Cl.[7] ......................... A61K 39/385; A61K 39/44
[52] U.S. Cl. .................................... 424/134.1; 424/178.1; 530/387.1; 530/388.22
[58] Field of Search .............................. 424/178.1, 93.21, 424/184.1, 193.1, 204.1, 234.1, 265.1, 274.1, 275.1, 809; 530/389.1

[56] References Cited

U.S. PATENT DOCUMENTS

| | | | |
|---|---|---|---|
| 4,261,973 | 4/1981 | Lee et al. | 424/78 |
| 4,650,675 | 3/1987 | Borel et al. | 424/85 |
| 4,902,495 | 2/1990 | Kaliner et al. | 424/1.1 |
| 5,116,964 | 5/1992 | Capon et al. | . |
| 5,169,627 | 12/1992 | Cunningham-Rundles | 424/85.91 |
| 5,277,894 | 1/1994 | Strauss et al. | 424/1.49 |
| 5,349,053 | 9/1994 | Landolfi | . |
| 5,428,130 | 6/1995 | Capon et al. | . |
| 5,455,165 | 10/1995 | Capon et al. | . |
| 5,514,582 | 5/1996 | Capon et al. | . |
| 5,534,496 | 7/1996 | Lee et al. | . |
| 5,541,087 | 7/1996 | Lo et al. | . |
| 5,565,335 | 10/1996 | Capon et al. | . |
| 5,658,762 | 8/1997 | Zanetti et al. | 435/69.6 |
| 5,698,679 | 12/1997 | Nemazee | . |
| 5,726,044 | 3/1998 | Lo et al. | . |

FOREIGN PATENT DOCUMENTS

| | | |
|---|---|---|
| 0 305 967 A2 | 9/1987 | European Pat. Off. . |
| 580171 | 1/1994 | European Pat. Off. . |
| WO 86/06635 | 11/1986 | WIPO . |
| WO 91/07987 | 6/1991 | WIPO . |
| WO91/08298 | 6/1991 | WIPO . |
| WO91/08773 | 6/1991 | WIPO . |
| WO94/14437 | 7/1994 | WIPO . |
| WO 94/15635 | 7/1994 | WIPO . |
| WO 93/17715 | 9/1993 | WIPO . |
| WO93/19660 | 10/1993 | WIPO . |
| WO 93/20834 | 10/1993 | WIPO . |
| WO93/21906 | 11/1993 | WIPO . |
| WO 96/22024 | 7/1996 | WIPO . |
| WO 98/34645 | 8/1998 | WIPO . |
| WO99/04813 | 2/1999 | WIPO . |

OTHER PUBLICATIONS

Squire, C.M. et al., Journal of Immunology, 4388–4396 (1994).
Gosselin, E.J. et al., 149:3477–3481 (1992).
Halina Borel et al., Journ. of Immunol. Methods: 159–168 (Sep. 20, 1990).
Roseli Farges al.—Fed. of European Bioche Biochem Soc. vol. 335 (3):305–308 (Oct. 12, 1993).
Nagy Mikael, et al., Lupus, vol. 3(173–179 (1994).
Malini Raghavan et al., Immunity, vol. 1:303–315 (Jul. 1994).
Victor Ghetie et al., Immunology Today, vol. 18 (12):592 (Dec. 1997).
International Search Report—PCT/US98/15395 (B0801/7117WO).
Supplementary Search Report—EP 96 90 3522.
Elson et al., J. Immunol. 133: 2892–2897 (1984), Cholera Toxin Feeding Did Not Induce Oral Tolerance in Mice and Abrogated Oral Tolerance to an Unrelated Protein Antigen.
Elson et al., J. Immunol. 135: 930–932 (1985), Genetic Control of the Murine Response to Cholera Toxin.
Lencer et al., J. Clin. Invest. 92: 2941–2951 (1993), Entry of Cholera Toxin into Polarized Human Intestinal Epithelial Cells: Identification of an Early Brefeldin A Sensitive Event Required for A1–Peptide Generation.
Lencer et al., J. Cell. Biol. 117: 1197–1209 (1992), Mechanism of Cholera Toxin Action on a Polarized Human Epithelial Cell Line: Role of Vesicular Traffic.
Mostov et al., Transcytosis. Cell 43: 389–390 (1985).
Langermann et al., J. Exp. Med. 180: 2277–2286 (1994), Protective Humoral Response Against Pneumoccal Infection in Mice Elicited by Recombinant Bacille Calmette–Guerin Vaccines Expressing Pneumoccal Surface Protein.
Service RF. "Triggering the first line of defense." Science 265: 1522–1524, Sep. 9, 1994.
Paul, W.F. (ed) Fundamental Immunology, 4th edition, pp. 1399–1401. Lippincott–Raven, Philadelphia, 1999.
Berryman et al., J. Histochem. Cytochem. 38(2):159–170 (1990), An Enhanced Method for Post–embedding Immunocytochemical Staining Which Preserves Cell Membranes.
Service, Science 265:1522–1524 (1994) Triggering the First Line of Defense.
Patel et al., FEBS Lett. 234(2):321–325 (1988), Fc Receptor–Mediated Transcytosis of IgG–coated Liposomes Across Epithelial Barriers.
Fritsche et al., J. Allergy Clin. Immunol. 93:778–786, (1994) Prevention of Allergic Sensitization to β–lactoglobulin with Conjugates Made of β–lactoglobulin Coupled to Isologous Immunoglobulin G.
Story et al., J. Exp. Med., 180:2377–2381 (1994), A Major Histocompatibility Complex Class I–like Fc Receptor Cloned from Human Placenta: Possible Role in Transfer of Immunoglobulin G from Mother to Fetus.
Kobayashi et al., J. Immunol. 146:68–74 (1991), The Molecular Configuration and Ultrastructural Locations of an IgG Fc Binding Site in Human Colonic Epithelium.

(List continued on next page.)

*Primary Examiner*—Thomas M. Cunningham
*Attorney, Agent, or Firm*—Wolf, Greenfield & Sacks, P.C.

[57] ABSTRACT

Methods and products for modulating an immune response are provided. Pharmaceutical preparations contain a conjugate of an antigen and a FcRn binding partner. The conjugates are administered to mammals in effective amounts to modulate the immune system by stimulating the immune response against the antigen or tolerizing the immune system to the antigen. The antigen may be characteristic of a pathogen, of an autoimmune disease or of an allergen.

12 Claims, No Drawings

OTHER PUBLICATIONS

Rabinovich et al., Science 265:1401–1404 (1994), Vaccine Technologies: View to the Future.

Simister et al., Nature 337:184–187 (1989), An Fc Receptor Structurally Related to MHC Class I Antigens.

Czerkinsky et al., Infect. Immun. 57:1072–1077 (1989), Oral Administration of a Streptoccal Antigen Coupled to Cholera.

Toxin B Submit Evokes Strong Antibody Responses in Salivary Glands and Extramucosal Tissues.

Elson et al., J. Immunol. 132:2736–2741 (1984), Generalized Systemic Mucosal Immunity in Mice After Mucosal Stimulation with Cholera Toxin.

Langermann et al., Nature 372:552–555 (1994), Systemic and Mucosal Immunity Induced by BCG Vector Expressing Outer–Surface Protein A of *Borrelia burgdorferi*.

Simister "Transport of Monomeric Antibodies Across Epithelia." pp. 57–73. In: Fc Receptors and the Action of Antibodies. H. Metzger, ed. (1990) American Society of Microbiology Press, Washington, D.C.

Burmeister et al. Nature 372: 379–383 (1994), Crystal Structure of the Complex of Rat Neonatal Fc Receptor with Fc.

Canfield et al., J. Exp. Med. 173: 1483–1491 (1991), The Binding Affinity of Human IgG for its High Affinity Fc Receptor Is Determined by Multiple Amino Acids in the Ch2 Domain and Is Modulated by the Hinge Region.

Woof et al., Mol. Immunol. 23: 319–330 (1986), Localisation of the Monocyte–binding region on Human Immunoglobulin G.

Lund et al., J. Immunol. 147:2657–2662 (1991) Human FcqRI and FcqRII Interact with Distinct but Overlapping Sites on Human IgG.

Huber et al., Mol. Biol. 230: 1077–1083 (1993) Crystallization and Stoichiometry of Binding of a Complex Between a Rat Intestinal Fc Receptor and Fc.

Guyer et al., J. Immunol. 117: 587–593 (1976) Immunoglobulin Binding by Mouse Intestinal Epithelial Cell Receptors.

Ahouse, et al., J. Immunol. 151: 6076–6088 (1993) A Mouse Class I–like Fc Receptor Encoded Outside the MHC.

Dertzbaugh, et al., Cholera Toxin as a Mucosal Adjuvant. In: Spriggs D.R. and Koff, W.C. eds. Topics in Vaccine Adjuvant Research, Boca Raton: CRC Press, pp. 119–131 (1990).

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

TGCTGGGCTG TGAACTG                    17

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

CGCTTTTAGC AGTCGGAA                    18

RECEPTOR SPECIFIC TRANSEPITHELIAL TRANSPORT OF IMMUNOGENS

GOVERNMENT SUPPORT

The work described herein was supported, in part, by National Institutes of Health Grant Nos. NIH DK-44319, NIH HO-27691 and NIH DK-48106. The U.S. Government has certain rights to this invention.

FIELD OF THE INVENTION

This invention relates in general to methods and products for initiating an immune response against an antigen, and in particular relates to transepithelial delivery of antigens to provoke tolerance and immunity.

BACKGROUND OF THE INVENTION

The immune system of a mammal develops during gestation and becomes active in the late mammalian fetus. Although active, it still might be characterized as 'immature'0 because it has not been challenged to any significant extent by antigens; the fetus is largely protected from antigens by the mother. This 'immature' immune system, however, is supplemented by the transfer of material immunoglobulin to the fetus (or in some cases to the neonate) to provide humoral immunity during the first weeks of independent life.

Rats and mice receive most maternal immunoglobulin G (IgG) as sucklings from colostrum and milk, although some is acquired prenatally. Cattle also receive IgG from colostrum. In rabbits, IgG is transported to the fetus across the yolk sac. Little is known about the transfer of IgG to the fetus or neonate in humans. Most evidence suggests that human mothers transfer humoral immunity to an offspring only before birth, although IgA transferred to a neonate via breast milk is believed to play a role in protecting the neonate against enteric infection.

The delivery of maternal IgG to the mammalian and/or neonate requires transport across an epithelial barrier which is largely impervious to macromolecules. The transport of macromolecules across such an epithelial barrier may occur by non-specific and specific receptor-mediated mechanisms. Receptor non-specific mechanisms are represented by paracellular sieving events, the efficiency of which are inversely related to the molecular weight of the transported molecule. Transport of macromolecules such as IgG across this paracellular pathway is highly inefficient. Descriptions of receptor-mediated transport of immunoglobulins through intestinal epithelial cells are limited thus far to the polymeric immunoglobulin receptor and the enterocyte receptor for IgG (a major histocompatibility complex (MHC) class I related Fc receptor). These two receptor systems differ in their specificity for immunoglobulin isotype, in their direction of immunoglobulin transport across the epithelial cell and in their tissue-specific expression. Both may play a role in molding the immature immune system.

The polymeric immunoglobulin receptor is expressed on the basolateral surfaces of enterocytes, hepatocytes and/or biliary duct epithelial cells. It transports polymeric IgA and IgM to the apical (luminal) surfaces, concentrating these immunoglobulins for antimicrobial defense and antigen exclusion.

The enterocyte receptor for IgG, which has homology to the MHC class I heavy chain and is associated with beta$_2$-microglobulin ($\beta_2$M), is expressed on neonatal enterocytes of the rat and mouse. IgG is transported transcellularly in a luminal to serosal direction across the intestinal epithelium of these rodent neonates. On the apical surface of the enterocyte, the Fc portion of IgG is bound to the enterocyte receptor at the relatively acidic pH of the lumen (about pH 6.0). Following transcytosis to the basolateral plasma membrane, discharge of the immunoglobulin occurs at the relatively neutral pH of the interstitial fluids (about pH 7.4). The rodent neonatal Fc receptor (FcRn) therefore could be responsible for delivery of maternal IgG to the neonate and as such may be responsible for the passive acquisition of IgG during this period.

In humans, maternal IgG is actively transported across the placenta. The receptor responsible for this transport has been sought for many years. Several IgG-binding proteins have been isolated from placenta. Fc$\gamma$RII was detected in placental endothelium and Fc$\gamma$RIII in syncytiotrophoblasts. Both of these receptors, however, showed a relatively low affinity for monomeric IgG. Recently, the isolation from placenta of a cDNA encoding a human homolog of the rat and mouse enterocyte receptor for IgG was reported. (Story, C. M. et al., J. Exp. Med., Vol. 180:2377–2381, December 1994) The complete nucleotide and deduced amino acid sequence is reported. This Fc receptor for IgG may be responsible for the transport of maternal IgG to the human fetus (and even possibly to the neonate), as the molecule is highly homologous over its open reading frame with the rat FcRn sequence (69% nucleotide identity and 65% predicted amino acid identity). So called passive immunization in the human fetus (and possibly in the human neonate) now may become better understood.

In contrast to passive immunization which involves supplementing a host's immune system with antibodies derived from another, active immunization involves stimulation of the host's own immune system to generate in vivo the desired immune response. The most widely practiced methods of active immunization in children and adults involve injections of an immunogen, once as an initial dose and then at least once again as a booster dose. These methods suffer many serious drawbacks, including the risks associated with the use of needles that can transmit diseases such as AIDS and hepatitis. (When tolerizing a patient against an allergen, the problems are compounded in that repeated injections over a long period of time often are required.) These methods also do not necessarily trigger adequately the first line of defense against many pathogens, that is, mucosal immunity. Mucous membranes line the airways, the reproductive system and the gastrointestinal tract, and this mucosal surface represents the first portal of entry for many diseases. An oral vaccine that is easy to deliver and that triggers mucosal immunity would be highly desirable.

Immunization using oral vaccines is problematic. Often little or no immune response is achieved. To enhance the immune response, antigens of interest have been coupled to carriers that are known to be strongly immunogenic. For example, researchers have delivered antigens using Bacille Calmette-Gurein (BCG) as a carrier; BCG is a bacterium originally used as an oral vaccine against tuberculosis. A problem with such carriers is that the patient will develop antibodies against the carrier itself, which can be troublesome if the carrier is used again for delivering a different antigen to the same patient. To date, no general strategy for oral vaccines has proven successful.

Immunoglobulin and portions thereof in the past have been conjugated to drugs and imaging agents to target and destroy cell populations and to extend the half-lives of certain agents. Immunotoxins are an example of such conjugates. Such conjugates, however, have never been proposed as useful for initiating an immune response.

A small body of work has focused on the tolerogenic capacity of immunoglobulins coupled to oligonucleotides or proteins characteristic of autoimmune diseases. (See PCT WO 91/08773). This work is based upon the notion that the induction of tolerance may be strongly influenced by carrier moieties and that immunoglobulin carriers appear to be strongly tolerogenic. Isologous IgG is the preferred carrier, and intravenous administration was the mode used for delivering the conjugates of IgG. Although this body of work extends for more than a decade, oral administration is mentioned only once and only for conjugates where IgA is the immunoglobulin carrier. Thus, although tolerogenic immunoglobulin conjugates are known in the art, such conjugates have never been suggested as agents for inducing a robust response against an antigen characteristic of a pathogen. (To the contrary, the art suggests that such conjugates, if anything, would tolerize a subject against a pathogen which would be highly undesirable). In addition, it never has been suggested that such conjugates would be effective tolerogens when the immunoglobulin is IgG and the mode of delivery is oral delivery.

SUMMARY OF THE INVENTION

The invention involves the discovery that antigens may be coupled to molecules that bind to the FcRn receptor, such as immunoglobulins, or portions thereof, and delivered across epithelial barriers by active transport through the enterocyte via FcRn receptors. The immunoglobulin or portion thereof binds to the FcRn receptor and acts as a carrier for the antigen as the immunoglobulin or portion thereof is transported across the epithelial barrier by FcRn mediated transport. The FcRn receptor is present in the human epithelial tissue of children and adults, and the invention therefore permits effective strategies for immunizing humans.

According to one aspect of the invention, a method for modulating the immune system of a mammal is provided. An effective amount of a conjugate of an antigen and a FcRn binding partner is administered to an epithelial barrier of a mammal in need of such immune modulation. The antigen is selected from the group consisting of: an antigen that is characteristic of a pathogen, an antigen that is characteristic of an autoimmune disease, and an antigen that is characteristic of an allergen. In preferred embodiments, the FcRn binding partner is non-specific IgG or a FcRn binding fragment of IgG. Most preferably the FcRn binding partner is an Fc fragment of IgG. It also is preferred that the antigen be covalently coupled to the FcRn binding partner. Preferably the conjugate is administered orally to the intestinal epithelium, in an aerosol to the lungs or intranasally. Such preparations may be nonaseptic. Supplementary potentiating agents, as described below, may be administered in addition.

According to another aspect of the invention, a pharmaceutical preparation is provided. The pharmaceutical preparation includes a conjugate of an antigen and a FcRn binding partner, wherein the antigen is selected from the group consisting of: an antigen that is characteristic of a pathogen, an antigen that is characteristic of an autoimmune disease, and an antigen that is characteristic of an allergen. The preferred FcRn binding partners are as described above. The conjugate is present in an amount effective for modulating the immune response of a mammal. The pharmaceutical preparation also includes a pharmaceutically acceptable carrier. When the antigen is characteristic of an autoimmune disease or an allergen, then the pharmaceutical preparations of the invention must be formulated in unit dosage form constructed and arranged for delivery to an epithelial carrier such as for oral delivery to the intestinal epithelium, aerosol delivery to the pulmonary epithelium and intranasal delivery to the nasal epithelium. Thus tablets containing IgG (or an FcRn binding portion thereof) coupled to any of the antigens as characterized above are embraced by the present invention.

The foregoing pharmaceutical preparations may be delivered together with supplementary potentiating agents including adjuvants, cytokines, bioadhesives and the like. The supplementary potentiating agents themselves may be coupled to a FcRn binding partner to facilitate the delivery of such agents across the epithelial barrier. Preferred modes of administration in general include oral dosages to the intestinal epithelium, aerosols to the lungs and intranasal dosages.

According to still another aspect of the invention, a method for making an immunomodulator is provided. The method involves covalently coupling an antigen or a supplementary potentiating agent to an FcRn binding partner, wherein the antigen or supplementary potentiating agent is selected as described above. The preferred FcRn binding partner also is as described above. The conjugates then can be used to prepare the pharmaceutical preparations for modulating a mammal's immune response as described above.

In yet another aspect of the invention, the conjugate including the antigen crosses the epithelial barrier in an amount at least double the extent that the antigen crosses the epithelial barrier in an unconjugated form. It thus is an object of the invention to develop a mechanism for increasing the ability of an antigen to cross an epithelial barrier.

Another object of the invention is to develop a new class of orally active immunogens and toleragens.

Another object of the invention is to develop improved methods for stimulating mucosal immunity.

These and other aspects of the invention are described in greater detail below.

DETAILED DESCRIPTION OF THE INVENTION

The invention involves the discovery that the human FcRn receptor is active in adult epithelial tissue and the discovery that FcRn binding partners such as IgG or Fc fragments can be used to transport other molecules, including antigens, across epithelial barriers. In this manner, FcRn binding partners such as IgG or an FcRn binding portion thereof can be used to deliver an antigen across an epithelial barrier to a subject's immune system, thereby initiating an immune response.

The invention is useful whenever it is desirable to enhance the delivery of an antigen across an epithelial barrier to the immune system. The invention thus may be used to deliver antigens across intestinal epithelial tissue, lung epithelial tissue and other mucosal surfaces including nasal surfaces, vaginal surfaces, colon surfaces and biliary tree surfaces. The invention may be used to modulate a subject's immune system such as by stimulating a humoral antibody response against an antigen, by stimulating T cell activity, or by stimulating tolerance to an antigen. As used herein, subject means: humans, primates, horses, cows, sheep, pigs, goats, dogs, cats, chickens and rodents.

The invention involves the formation of a conjugate of an FcRn binding partner and an antigen. By conjugate it is meant two entities bound to one another by any physiochemical means, including hydrophobic interaction between an antigen and the non-specific hydrophobic portions of an antibody molecule, antibody-antigen specific binding and covalent coupling. The nature of the preferred bonding will depend, among other things, upon the mode of administration and the pharmaceutical carriers used to deliver the conjugate to the selected epithelial barrier. For example, some bonds are not as well suited as others to withstand certain environments such as the stomach, but can be protected therefrom by delivery systems which bypass the stomach. It, of course, is important that the bond between the FcRn binding partner and the antigen be of such a nature that it does not destroy the ability of the FcRn binding partner to bind to the FcRn receptor. Such bonds are well known to those of ordinary skill in the art; examples are provided in greater detail below. The conjugate further may be formed as a fusion protein, also discussed in greater detail below.

An FcRn binding partner means any entity that can be specifically bound by the FcRn receptor with consequent active transport by the FcRn receptor of the FcRn binding partner. As mentioned above, the FcRn receptor has been isolated for several mammalian species, including humans. The sequence of the human FcRn, rat FcRn and mouse FcRn may be found in Story, C. M. et al, J. Exp. Med., vol. 180:2377–2381, December 1994. The FcRn receptor molecule now is well characterized. The FcRn receptor binds IgG (but not other immunoglobulin classes such as IgA, IgD, IgM and IgE) at a relatively lower pH, actively transports the IgG transcellularly in a luminal to serosal direction, and then releases the IgG at a relatively higher pH found in the interstitial fluids. As will be recognized by those of ordinary skill in the art, FcRn receptors can be isolated by cloning or by affinity purification using, for example, monoclonal antibodies. Such isolated FcRn receptors then can be used to identify and isolate FcRn binding partners, as described below.

FcRn binding partners include whole IgG, the Fc fragment of IgG and other fragments of IgG that include the complete binding region for the FcRn receptor. The region of the Fc portion of IgG that binds to the FcRn receptor has been described based upon X-ray crystallography (Burmeister, W. P. et al., *Nature*, 1994; 372:379–378.) The major contact area of Fc with the FcRn receptor is near the junction of the $C_H2$ and $C_H3$ domains. Potential contacts are residues 248, 250–257, 272, 285, 288, 290–291, 308–311 and 314 in $C_H2$ and 385–387, 428 and 433–436 in $C_H3$. (These sites are distinct from those identified by subclass comparison or by site-directed mutagenesis as important for Fc binding to leukocyte FcγRI and FcγRII.) The foregoing Fc–FcRn contacts are all within a single Ig heavy chain. It has been noted previously that two FcRn receptors can bind a single Fc molecule. The crystallographic data suggest that in such a complex, each FcRn molecule binds a single polypeptide of the Fc homodimer.

Given the foregoing information, those of ordinary skill in the art will readily recognize that the Fc region of IgG can be modified according to well-recognized procedures such as site-directed mutagenesis and the like to yield modified IgG or modified Fc fragments or portions thereof that will be bound by the FcRn receptor. Such modifications include modifications remote from the FcRn contact sites as well as modifications within the contact sites that preserve or even enhance binding. In addition, other binding partners can be identified and isolated. Antibodies or portions thereof specific for the FcRn receptor and capable of being transported by FcRn once bound can be identified and isolated using well established techniques. Likewise, random generated molecularly diverse libraries can be screened and molecules that are bound and transported by FcRn receptors can be isolated using conventional techniques. It is not intended that the invention be limited by the selection of any particular FcRn binding partner. Where the binding partner is IgG or a FcRn binding portion thereof, the IgG or portion thereof may be prepared according to conventional procedures as described in greater detail below.

The FcRn binding partner is conjugated with an antigen. An antigen as used herein falls into three classes: 1) antigens that are characteristic of a pathogen; 2) antigens that are characteristic of an autoimmune disease; and 3) antigens that are characteristic of an allergen. Antigens in general include polysaccharides, glycolipids, glycoproteins, peptides, proteins, carbohydrates and lipids from cell surfaces, cytoplasm, nuclei, mitochondria and the like.

Antigens that are characteristic of pathogens include antigens derived from viruses, bacteria, parasites or fungi. Examples of important pathogens include vibrio cholerae, enterotoxigenic escherichia coli, rotavirus, clostridium difficile, shigella species, salmonella typhi, parainfluenza virus, influenza virus, streptococcus pneumoniae, borella burgdorferi, HIV, streptococcus mutans, plasmodium falciparum, staphylococcus aureus, rabies virus and Epstein-Barr virus.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

Bacteria in general include but are not limited to: *P. aeruginosa; E. coli*; Klebsiella sp.; Serratia sp.; Pseudomonas sp.; *P. cepacia*; Acinetobacter sp.; *S. epidermis; E. faecalis; S. pneumoniae; S. aureus*; Haemophilus sp.; Neisseria sp.; *N. meningitidis*; Bacteroides sp.; Citrobacter sp.; Branhamella sp.; Salmonella sp.; Shigella sp.; *S. pyogenes*; Proteus sp.; Clostridium sp.; Erysipelothrix sp.; Lesteria sp.; *Pasteurella multocida*; Streptobacillus sp.; Spirillum sp.; Fusospirocheta sp.; *Treponema pallidum*; Borrelia sp.; Actinomycetes; Mycoplasma sp.; Chlamydia sp.; Rickettsia sp.; Spirochaeta; Legionella sp.; Mycobacteria sp.; Ureaplasma sp.; Streptomyces sp.; Trichomoras sp.; and *P. mirabilis*.

Parasites include but are not limited to: *Plasmodium falciparum, P. vivax, P. ovale, P. malaria; Toxoplasma gondii; Leishmania mexicana, L. tropica, L. major, L. aethiopica, L. donovani; Trypanosoma cruzi, T. brucei; Schistosoma mansoni, S. haematobium, S.japonium; Trichinella spiralis; Wuchereria bancrofti; Brugia malayi; Entamoeba histolytica; Enterobius vermiculoarus; Taenia solium, T. saginata; Trichomonas vaginatis, T. hominis, T. tenax; Giardia lamblia; Cryptosporidium parvum; Pneumocytis carinii; Babesia bovis, B. divergens, B. microti; Isospora belli, I. hominis; Dientamoeba fragilis; Onchocerca volvulus; Ascaris lumbricoides; Necator americanis; Ancylostoma duodenale; Strongyloides stercoralis; Capillaria philippinensis; Angiostrongylus cantonensis; Hymenolepis nana; Diphyllobothrium latum; Echinococcus granulosus, E. multilocularis; Paragonimus westermani, P. caliensis; Chlonorchis sinensis; Opisthorchis felineus, O. viverrini; Fasciola hepatica; Sarcoptes scabiei; Pediculus humanus; Phthirius pubis*; and *Dermatobia hominis*.

Fungi in general include but are not limited to: *Cryptococcus neoformans; Blastomyces dermatitidis; Ajellomyces*

*dermatitidis; Histoplasma capsulatum; Coccidioides immitis;* Candida species, including *C. albicans, C. tropicalis, C. parapsilosis, C. guilliermondii and C. krusei;* Aspergillus species, including *A. fumigatus, A. flavus* and *A. niger;* Rhizopus species; Rhizomucor species; Cunninghammella species; Apophysomyces species, including *A. saksenaea, A. mucor* and *A. absidia; Sporothrix schenckii; Paracoccidioides brasiliensis; Pseudallescheria boydii; Torulopsis glabrata;* and Dermatophytes species.

Antigens that are characteristic of autoimmune disease typically will be derived from the cell surface, cytoplasm, nucleus, mitochondria and the like of mammalian tissues. Examples include antigens characteristic of uveitis (e.g. Santigen), diabetes mellitus, multiple sclerosis, systemic lupus erythematosus, Hashimoto's thyroiditis, myasthenia gravis, primary myxoedema, thyrotoxicosis, rheumatoid arthritis, pernicious anemia, Addison's disease, scleroderma, autoimmune atrophic gastritis, premature menopause (few cases), male infertility (few cases), juvenile diabetes, Goodpasture's syndrome, pemphigus vulgaris, pemphigoid, sympathetic opthalmia, phacogenic uveitis, autoimmune haemolytic anemia, idiopathic thrombocytopenic purpura, idiopathic leucopenia, primary biliary cirrhosis (few cases), ulcerative colitis, Sjogren's syndrome, Wegener's granulomatosis, poly/dermatomyositis, and discoid lupus erythromatosus.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include the urushiols (pentadecylcatechol or heptadecylcatechol) of Toxicodendron species such as poison ivy, poison oak and poison sumac, and the sesquiterpenoid lactones of ragweed and related plants.

In the cases of protein and peptide antigens, covalent linking to an FcRn partner is intended to include linkage by peptide bonds in a single polypeptide chain. Established methods (Sambrook, Ausubel) would be used to engineer DNA encoding a fusion protein comprised of the antigenic peptide or protein and an FcRn partner. This DNA would be placed in an expression vector and introduced into bacterial or eukaryotic cells by established methods. The fusion protein would be purified from the cells for from culture medium by established methods.

When administered, the conjugates of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents. Thus, "cocktails" including the conjugates and the agents are contemplated. The agents themselves may be conjugated to FcRn binding partners to enhance delivery of the agents across the epithelial barriers.

The conjugates of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmaceutically acceptable salts include, but are not limited to, those prepared from the following acids: hydrochloric, hydrobromic, sulphuric, nitric, phosphoric, maleic, acetic, salicyclic, p-toluene sulphonic, tartaric, citric, methane sulphonic, formic, malonic, succinic, naphthalene-2-sulphonic, and benzene sulphonic. Also, pharmaceutically acceptable salts can be prepared as alkyline metal or alkyline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); sodium bicarbonate (0.5–1.0% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% W/V).

The term "carrier" as used herein, and described more fully below, means one or more solid or liquid filler, dilutants or encapsulating substances which are suitable for administration to a human or other mammal. The "carrier" may be an organic or inorganic ingredient, natural or synthetic, with which the active ingredient is combined to facilitate administration.

The components of the pharmaceutical compositions are capable of being comingled with the conjugates of the present invention, and with each other, in a manner such that there is no interaction which would substantially impair the desired pharmaceutical efficiency. The components of oral drug formulations include diluents, binders, lubricants, glidants, disintegrants, coloring agents and flavoring agents. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

The term "adjuvant" is intended to include any substance which is incorporated into or administered simultaneously with the conjugates of the invention and which nonspecifically potentiates the immune response in the subject. Adjuvants include aluminum compounds, e.g., gels, aluminum hydroxide and aluminum phosphate, and Freund's complete or incomplete adjuvant (in which the conjugate is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U) leutinan, pertussis toxin, cholera toxin, lipid A, saponins and peptides, e.g. muramyl dipeptide. Rare earth salts, e.g., lanthanum and cerium, may also be used as adjuvants. The amount of adjuvants depends on the subject and the particular conjugate used and can be readily determined by one skilled in the art without undue experimentation.

Other supplementary immune potentiating agents, such as cytokines, may be delivered in conjunction with the conjugates of the invention. The cytokines contemplated are those that will enhance the beneficial effects that result from administering the immunomodulators according to the invention. Cytokines are factors that support the growth and maturation of cells, including lymphocytes. It is believed that the addition of cytokines will augment cytokine activity stimulated in vivo by carrying out the methods of the invention. The preferred cytokines are interleukin (IL)-1, IL-2, gamma-interferon and tumor necrosis factor α. Other useful cytokines are believed to be IL-3, IL-4, IL-5, IL-6, IL-7, IL-8, IL-9, IL-10, IL-11, IL-12, IL-13, erythropoietin, leukemia inhibitory factor, oncostatin-M, ciliary neurotrophic factor, growth hormone, prolactin, CD40-ligand, CD27-ligand, CD30-ligand, alpha-interferon, beta-interferon, and tumor necrosis factor-β. Other cytokines known to modulate T-cell activity in a manner likely to be useful according to the invention are colony stimulating factors and growth factors including granulocyte and/or macrophage stimulating factors (GM-CSF, G-CSF and CSF-1) and platelet derived, epidermal, insulin-like, transforming and fibroblast growth factors. The selection of the particular cytokines will depend upon the particular modulation of the immune system that is desired. The activity of cytokines on particular cell types is known to those of ordinary skill in the art.

The precise amounts of the foregoing cytokines used in the invention will depend upon a variety of factors, including the conjugate selected, the dose and dose-timing selected, the mode of administration and the characteristics of the subject. The precise amounts selected can be determined without undue experimentation, particularly since a threshold amount will be any amount which will enhance the desired immune response. Thus, it is believed that nanogram to milligram amounts are useful, depending upon the mode of delivery, but that nanogram to microgram amounts are likely to be most useful because physiological levels of cytokines are correspondingly low.

The preparations of the invention are administered in effective amounts. An effective amount is that amount of a conjugate that will alone, or together with further doses, stimulate an immune response as desired. This may involve the stimulation of a humoral antibody response resulting in an increase in antibody titer in serum, improved mucosal immunity, a clonal expansion of cytotoxic T lymphocytes or tolerance to an antigen, including a self antigen. It is believed that doses ranging from 1 nanogram/kilogram to 100 milligrams/kilogram, depending upon the mode of administration, will be effective. The preferred range is believed to be between about 500 nanograms and 500 micrograms/kilogram, and most preferably between 1 microgram and 100 micrograms/kilogram. The absolute amount will depend upon a variety of factors, including the conjugate selected, the immune modulation desired, whether the administration is in a single or multiple doses, and individual patient parameters including age, physical condition, size and weight. These factors are well known to those of ordinary skill in the art and can be addressed with no more than routine experimentation.

A variety of administration routes are available. The particular mode selected will depend, of course, upon the particular conjugate selected, the particular condition being treated and the dosage required for therapeutic efficacy. The methods of this invention, generally speaking, involve delivering the conjugates of the invention to an epithelial surface. Preferred modes of administration are oral, intrapulmonary, intrabiliary and intranasal.

Compositions may be conveniently presented in unit dosage form and may be prepared by any of the methods well known in the art of pharmacy. All methods include the step of bringing the conjugate into association with a carrier which constitutes one or more accessory ingredients. In general, the compositions are prepared by uniformly and intimately bringing the conjugate into association with a liquid carrier, a finely divided solid carrier, or both, and then, if necessary, shaping the product.

Other delivery systems can include time-release, delayed release or sustained release delivery systems. Such systems can avoid repeated administrations of the conjugates of the invention, increasing convenience to the subject and the physician. Many types of release/delivery systems are available and known to those of ordinary skill in the art. They include polymer based systems such as polylactic and polyglycolic acid, polyanhidrides and polycaprolactone; wax coatings, compressed tablets using conventional binders and excipients, and the like. Bioadhesive polymer systems to enhance delivery of a material to the intestinal epithelium are known and described in published PCT application WO 93/21906. Capsules for delivering agents to the intestinal epithelium also are described in published PCT application WO 93/19660.

EXAMPLES

Materials

Abbreviations

BSA, bovine serum albumin; cDNA, complementary deoxyribonucleic acid; CT-B, cholera toxin B subunit; DMEM, Dulbecco's modified Eagle's medium; DMSO, dimethyl sulfoxide; DOC, desoxycholate; ECL, enhanced chemiluminescence; ELISA, enzyme linked immunosorbant assay; HBSS, Hanks' balanced salt solution without calcium or magnesium; HEPES, N-[2-hydroxyethyl]piperazine-N'-[2-ethanesulfonic acid]; hGH, human growth hormone; IEC, intestinal epithelial cells; KI, potassium iodide; MHC, major histocompatibility complex; NaOH, sodium hydroxide; $NH_4Cl$, ammonium chloride; NHS-rhodamine, N-hydroxysuccinimidyl-rhodamine; RNA, ribonucleic acid; RT-PCR, reverse transcriptase-polymerase chain reaction; SATA, N-succinimidyl S-acetylthioacetate; SDS-PAGE, sodium dodecyl sulfate-polyacrylamide gel electrophoresis; sulfo-LC-SPDP, sulfosuccinimidyl 6-[3-(2-pyridyldithio) propionamide] hexanoate; sulfo-NHS-biotin, sulfosuccinimidobiotin; sulfo-SMCC, sulfosuccinimidyl 4-(N-maleimidomethyl) cyclo-hexane-1-carboxylate.

Chemicals cDNA Cycle Kits was purchased from Invitrogen (San Diego, Calif.). Taq polymerase was purchased from Perkin-Elmer Cetus (Norwalk, Conn.). CircumVent™ Kits were purchased from New England Biolabs (Beverly, Mass.). Radionuclides and radioactive chemicals were purchased from DuPont/NEN (Boston, Mass.). HBSS- and DMEM were purchased from GIBCO/Life Technologies (Gaithersburg, Md.). RPMI 1640 was purchased from Cellgro (Herndon, Va.). L-glutamine was purchased from Cellgro. Protein A-Sepharose was purchased from Pharmacia Biotech (Piscataway, N.J.). Streptavidin-horseradish peroxidase, sulfo-LC-SPDP, sulfo-NHS-biotin, sulfo-SMCC, SATA and immobilized ficin were purchased from Pierce (Rockford, Ill.). Balb/c mice were purchased from Charles River Laboratories (Wilmington, Mass.). ECL kits were purchased from Amersham (Arlington Heights, Ill.). Plasmin, AvidChrom-protein A, protein G-Sepharose, BSA, cholera toxin B subunit, anti-hGH antibodies and all other chemicals were purchased from Sigma (St. Louis, Mo.).

Example 1
Expression of FcRn mRNA in Human Intestinal Epithelial Primary Cells and Cell Lines Total RNA was extracted from adult human enterocytes by standard methodology well known in the art (Sambrook et al., ibid.). One microgram of RNA from each cell type was used as a template to prepare the cDNA substrate for reverse transcriptase-polymerase chain reaction (RT-PCR) using a cDNA Cycle Kit (Invitrogen, San Diego, Calif.). Thirty cycles of PCR were performed on the cDNA using Taq polymerase (Perkin-Elmer Cetus, Norwalk, Conn.) according to the manufacturer's instructions using primers TGCTGGGCTGTGAACTG (SEQ ID NO:1 and CGCTTT-TAGCAGTCGGAA (SEQ ID NO:2. The PCR cycle conditions were: denaturation at 94° C. for one minute, annealing at 55° C. for two minutes and extension at 72° C. for three minutes. Amplification products were resolved by electrophoresis on a 1.5% agarose gel and visualized by ethidium bromide staining, which showed the presence of the expected approximately 800 base pair amplification product in all samples except the adult colonic epithelial cells. To confirm the identity of the RT-PCR amplification product, the DNA band was excised from the agarose gel, subcloned into pCR II (Invitrogen, San Diego, Calif.) and sequenced using a Prism N dye-deoxy terminator cycle sequencing kit (Applied Biosystems, Foster City, Calif.) using primers from both vector and human FcRn sequence. Reaction products were analyzed on an Applied Biosystems sequencer. The sequence of the amplification products exactly matched the FcRn gene sequence, confirming the identity of the expressed gene.

Example 2
Detection of FcRn mRNA by Northern Blot

To confirm the expression of FcRn in human intestinal epithelial cells and cell lines, a Northern blot was prepared using the RNA samples prepared as described in Example 1 from adult human enterocytes, and from two human adenocarcinoma cell lines of colonic origin, CaCO-2 and HT-29. The RNA samples were resolved by formaldehyde/agarose gel electrophoresis and transferred to a nylon membrane by standard procedures (Sambrook or Ausubel). The membrane was probed using a $^{32}$P-radiolabeled 120 base pair probe from the 3' untranslated region of FcRn by standard methods. Autoradiograms of the Northern blot demonstrated the presence of the 1.5 kilobase hFcRn transcript in the enterocytes and both cell lines. Therefore, the expression of FcRn in human adult intestinal epithelial cells and cell lines was demonstrated by two different methods of RNA detection.

Example 3
Labeling and Immunoprecipitation of the MHC-Class I Related Fc Receptor (FcRn) from Intestinal Epithelial Cells The expression of FcRn in human intestinal epithelial cells was confirmed by immunoprecipitation of the protein. Caco-2 cells were labeled metabolically using $^{35}$S-methionine (DuPont/NEN, Boston, Mass.) and proteins were extracted by methods well known in the art (Harlow and Lane, *Antibodies: A Laboratory Manual*). A polyclonal rabbit anti-rat MHC class I related FcR heavy chain specific antiserum bound to protein-A-sephorose was used to immunoprecipitate FcRn from the cell extracts using standard methods (FcRn can be purified by well established methods, Simister and Rees 1985, European J. Immunology, 15:733–8, and used to immunize rats followed by collection of serum, Harlow and Lane, supra.). Immunoprecipitates were resolved by SDS-PAGE and visualized by autoradiography. A 48 kilodalton FcRn protein was observed, confirming expression observed at the RNA level.

Example 4
Expression of FcRn Protein on the Cell Surface of Human Intestinal Epithelial Cells About $3 \times 10^7$ HT-29 intestinal epithelial cells were detached from tissue culture plates by nonenzymatic methods and were washed four times with ice cold Hanks' balanced salt solution containing no calcium or magnesium (HBSS-,GIBCO/Life Technologies, Gaithersburg, Md.). To label cell surface proteins, the washed cells were incubated twice for 20 minutes with 1.5 ml of 0.5 mg/ml sulfo-NHS-biotin (Pierce, Rockford, Ill.) in DMSO. Labeled cells were washed five times with 50 mM $NH_4Cl$, incubated 20 minutes with 10 ml of RPMI 1640 (Cellgro, City, State) containing 1 mM L-glutamine (Mediatech, Washington, D.C.), and washed four times with HBSS-. The cells were lysed, then precleared overnight with protein A-Sepharose beads (Pharmacia Biotech, Piscataway, N.J.) using standard techniques well known in the art. SDS and desoxycholic acid (DOC) were added to the supernatants to final concentrations of 0.1% and 0.5%, respectively. Lysates were precleared with normal rabbit serum and immunoprecipitated with polyclonal rabbit anti-rat MHC class I related FcR antibody by methods well known in the art. Immunoprecipitates were resolved by SDS-PAGE and transferred to nitrocellulose membranes. The nitrocellulose membrane was processed for incubation with 1:10,000 diluted streptavidin-horseradish peroxidase (Pierce, Rockford Ill.) as recommended by the manufacturer. The membrane was then processed for detection of bound horseradish peroxidase using an ECL kit (Amersham, Arlington Heights, Ill.). Light emitted by cleavage of the chemiluminescent substrate was detected by exposure of the membrane to light-sensitive film. The film exposures showed that FcRn was expressed on the surface of HT-29 intestinal epithelial cells.

Example 5
Functional Activity of Human FcRn on the Cell Surface of Intestinal Epithelial Cells To show that the FcRn expressed on the cell surface of intestinal epithelial cells was functional, Caco-2 cells and human adult jejunal intestinal epithelial cells (IECs) were tested for the ability to bind Fc fragment of antibody. Caco-2 and jejunal IECs were distributed to microcentrifuge tubes ($2 \times 10^6$ cells per tube) and pelleted at 2000 rpm for 2–3 minutes at 4° C. Cell pellets were washed once in DMEM containing 20 mM HEPES, pH 6.0 or pH 8.0 at 4° C. and resuspended in 0.2 ml of the same medium. The cell suspensions were transferred to 12 well plates for assay.

$^{125}$I-Fc fragment (200 ng/ml, $4 \times 10^{-9}$M) in DMEM containing 20 mM HEPES, 1.0 mM KI and 0.1% fish gelatin, pH 6.0 or pH 8.0 with or without 0.5 mg/ml unlabeled human IgG ($3.3 \times 10^{-6}$M) was added to each well. The cells were allowed to bind IgG or Fc at 37° C. for two hours in a 5% $CO_2$ humidified atmosphere. Cells were transferred to microcentrifuge tubes and pelleted at 2000 rpm for 2–3 minutes at 4° C. Unbound 125I-Fc was removed by washing the cell pellets once with cold DMEM containing 20 mM HEPES, pH 6.0 or pH 8.0 at 4° C. Cells were disrupted in 0.5 ml 0.1 M NaOH and the resulting solution transferred to scintillation vials. $^{125}$I was quantified using a CliniGamma 1272 gamma counter (LKB Wallac, Piscataway, N.J.). Both Caco-2 cells and human adult jejunum IECs specifically bound $^{125}$I-Fc at pH 6.0 but not at pH 8.0, demonstrating functional pH-dependent binding as observed for rat neonatal FcRn and cloned human FcRn (Story et al., *J. Exp. Med.* 180:2377–2381; December 1994).

Example 6
Preparation of Human Immunoglobulin G

Non-specific purified immunoglobulin G from human, mouse, rat, goat, pig, cow, and other species may be purchased from commercial vendors such as Sigma Chemical Co., Pierce Chemical, HyClone Laboratories, ICN Biomedicals and Organon Teknika-Cappel.

Immunoglobulin G also may be isolated by ammonium sulfate precipitation of precipitation of blood serum. The protein precipitate is further fractionated by ion exchange chromatography or gel filtration chromatography, to isolate substantially purified non-specific IgG. By non-specific IgG it is meant that no single specificity within the antibody population or pool is dominant.

Immunoglobulin G also may be purified from blood serum by adsorption to protein A attached to a solid support such as protein A-Sepharose (Pharmacia), AvidChrom-Protein A (Sigma), or protein G-Sepharose (Sigma). Other methods of purification of IgG are well known to persons skilled in the art and may be used for the purpose of isolation of non-specific IgG.

Example 7
Preparation of Human Immunoglobulin G Fc Fragment

To prepare the Fc fragments of human IgG, IgG isolated as in example 6 is subjected to digestion with immobilized papain (Pierce) according to the manufacturer's recommended protocol. Other proteases that digest IgG to produce intact Fc fragments that can bind to Fc receptors, e.g. plasmin (Sigma) or immobilized ficin (Pierce), are known to skilled artisans and may be used to prepare Fc fragments. The digested immunoglobulin then is incubated with an affinity matrix such as protein A-Sepharose or protein G-Sepharose. Non-binding portions of IgG are eluted from the affinity matrix by extensive washing in batch or column format. Fc fragments of IgG then are eluted by addition of a buffer that is incompatible with Fc-adsorbant binding. Other methodologies effective in the purification of Fc fragments also may be employed.

Example 8
Conjugation of Compounds to Human Immunoglobulin Fc Fragments

To deliver compounds via the FcRn transport mechanism, such compounds can be coupled to whole IgG or Fc fragments. The chemistry of cross-linking and effective reagents for such purposes are well known in the art. The nature of the crosslinking reagent used to conjugate whole IgG or Fc fragments and the compound to be delivered is not restricted by the invention. Any crosslinking agent may be used provided that a) the activity of the compound is retained, and b) binding by the FcRn of the Fc portion of the conjugate is not adversely affected.

An example of an effective one-step crosslinking of Fc and a compound is oxidation of Fc with sodium periodate in sodium phosphate buffer for 30 minutes at room temperature, followed by overnight incubation at 4° C. with the compound to be conjugated. Conjugation also may be performed by derivatizing both the compound and Fc fragments with sulfosuccinimidyl 6-[3-(2-pyridyldithio) propionamide]hexanoate (sulfo-LC-SPDP, Pierce) for 18 hours at room temperature. Conjugates also may be prepared by derivatizing Fc fragments and the desired compound to be delivered with different crosslinking reagents that will subsequently form a covalent linkage. An example of this reaction is derivatization of Fc fragments with sulfosuccinimidyl 4-(N-maleimidomethyl) cyclo-hexane-1-carboxylate (Sulfo-SMCC, Pierce) and the compound to be conjugated to Fc is thiolated with N-succinimidyl S-acetylthioacetate (SATA). The derivatized components are purified free of crosslinker and combined at room temperature for one hour to allow crosslinking. Other crosslinking reagents comprising aldehyde, imide, cyano, halogen, carboxyl, activated carboxyl, anhydride and maleimide functional groups are known to persons of ordinary skill in the art and also may be used for conjugation of compounds to Fc fragments. In all of the above crosslinking reactions it is important to purify the derivatized compounds free of crosslinking reagent. It is important also to purify the final conjugate substantially free of unconjugated reactants. Purification may be achieved by affinity, gel filtration or ion exchange chromatography based on the properties of either component of the conjugate. A particularly preferred method is an initial affinity purification step using protein A-Sepharose to retain Fc and Fc-compound conjugates, followed by gel filtration or ion exchange chromatography based on the mass, size or charge of the Fc conjugate. The initial step of this purification scheme ensures that the conjugate will bind to FcRn which is an essential requirement of the invention.

Example 9
IgG-Facilitated Delivery of Foreign Antigen Across the Intestinal Epithelial Barrier To test the ability of Fc binding partner-antigen conjugates to be transported across epithelial barriers, foreign antigens are conjugated to IgG molecules for administration to mice. A convenient foreign antigen is the fluorescent dye rhodamine, since it may be visualized in frozen semi-thin sections of intestinal epithelium. Rhodamine is covalently linked to non-specific mouse IgG, prepared as described in Example 6, cholera toxin B subunit (Sigma) and ovalbumin (Sigma) by incubation with succinyl-rhodamine (Molecular Probes, Eugene, Oreg.) as recommended by the manufacturer. The IgG-rhodamine conjugate is purified by protein G-Sepharose affinity chromatography. After dialysis to remove unconjugated succinyl-rhodamine, cholera toxin B (CT-B)-rhodamine and ovalbumin-rhodamine conjugates are purified by gel filtrations or ion exchange chromatography. Fractions of the eluate are assayed for the presence of conjugates by determining fluorescence. Functional binding of the IgG and CT-B subunit conjugates may be tested by binding to FcRn and ganglioside GMl, respectively. Cholera toxin B-rhodamine and ovalbumin-rhodamine serve as positive and negative controls, respectively.

Balb/c mice are administered 0.2 nanomoles of the three rhodamine cojugates described above, with or without 0.2 nanomoles unlabeled cholera toxin as a non-specific adjuvant, by intragastric administration in the presence of 75 micromoles $NaHCO_3$ and 20 mg/ml soybean trypsin inhibitor to inhibit gastric degradation. After 6 hours the mice are sacrificed and intestine is removed, frozen and processed for semi-thin sectioning. Sections of the intestinal epithelium are illuminated on a fluorescent microscope and examined for intracellular fluorescence. The presence of fluorescence in intestinal epithelial cells of mice fed IgG-rhodamine indicates that the IgG conjugates are effectively transported in an apical to basolateral direction across the intestinal epithelial barrier. FcRn is capable of transporting immunogens as conjugates with FcRn binding partners.

Example 10

Mouse Mucosal Immune Response to Orally Delivered Antigen-IgG Conjugate Via FcRn-Mediated Transcytosis Transgenic mice homozygous for deletion of $\beta_2$-microglobulin (a critical component of Fc-receptor function) and their normal wild-type litter mates are used for studies of generation of a mucosal immune response. If rhodamine-IgG elicits a mucosal immune response by binding to apical membrane Fc receptors, a positive immune response should be found in wild-type but not $\beta_2$-microglobulin "knockout" mice. In contrast, rhodamine-cholera toxin B subunit (CT-B) should elicit a positive immune response in both wild type and "knockout" mice as transcytosis of CT-B across the epithelial barrier is not dependent on binding to apical membrane Fc receptors. Rhodamine-ovalbumin does not enter transcytotic vesicles (but may enter intestinal epithelia by fluid phase endocytosis) and should not elicit an immune response in any mice.

Three groups of wild type and $\beta_2$-microglobulin knockout mice are orally immunized with the three rhodamine conjugates described in Example 9. Parallel experiments are conducted with the addition of 0.2 nanomoles of cholera toxin as non-specific adjuvant. Equimolar quantities of the rhodamine conjugates are administered intragastrically. The mice are "immunized" by this method every ten days for a total of three times. Two weeks after the third oral immunization the mice are sacrificed and the rhodamine-specific immune response is determined by ELISA on gut secretions and serum by standard methodology. Anti-rhodamine serum immunoglobulins are most evident in the wild type mice fed rhodamine conjugates of CT-B and IgG. Knockout mice lacking $\beta_2$-microglobulin generate a mucosal immune response to rhodamine-CT-B but not to rhodamine-IgG, indicating that receptor-mediated transcytosis plays an essential role in the mucosal immune response. The control rhodamine-ovalbumin conjugate elicits little or no immune response in either the wild type or the $\beta_2$-microglobulin knockout mice.

Those skilled in the art will be able to recognize or ascertain with no more than routine experimentation numerous equivalents to the specific products and processes described above. Such equivalents are considered to be within the scope of the invention and are intended to be covered by the following claims.

We claim:

1. A method for activating or suppressing a systemic immune response in a mammal comprising:
   administering to the luminal side of an epithelial barrier of an epithelial tissue expressing FcRn receptor an effective amount of a conjugate of an FcRn binding partner and an antigen selected from group consisting of:
   an antigen characteristic of a pathogen,
   an antigen characteristic of an autoimmune disease, and
   an antigen characteristic of an allergen.

2. The method of claim 1 wherein the conjugate is administered orally to the intestinal epithelium.

3. The method of claim 1 wherein the conjugate is administered in an aerosol to the lungs.

4. The method of claim 1 wherein the FcRn binding partner is a non-specific IgG or a FcRn binding fragment of IgG.

5. The method of claim 1 wherein the FcRn binding partner is an Fc fragment of IgG.

6. The method of any one of claims 1, 2, 3, 4, and 5, wherein the antigen is covalently coupled to the FcRn binding partner.

7. The method of any one of claims 1, 2, 3, 4, and 5, wherein the antigen is characteristic of an pathogen and wherein the conjugate is administered in an amount effective for activating an immune response.

8. The method of claim 7 wherein the antigen is covalently coupled to the FcRn binding partner.

9. The method of any one of claims 1, 2, 3, 4, and 5, wherein the antigen is selected from the group consisting of:
   an antigen that is characteristic of an autoimmune disease, and
   an antigen that is characteristic of an allergen, and wherein
   the conjugate is administered in an amount effective to suppress the immune response.

10. The method of claim 1, wherein the mammal is a human.

11. The method of claim 10, wherein the human is an adult.

12. The method of claim 10, wherein the human is a child.

* * * * *